(12) United States Patent
Dahlberg

(10) Patent No.: US 8,099,177 B2
(45) Date of Patent: Jan. 17, 2012

(54) IMPLANTABLE MEDICAL LEAD AND METHOD FOR THE MANUFACTURE THEREOF

(75) Inventor: Kenneth Dahlberg, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 495 days.

(21) Appl. No.: 12/280,500

(22) PCT Filed: Mar. 2, 2006

(86) PCT No.: PCT/SE2006/000275
§ 371 (c)(1),
(2), (4) Date: Nov. 25, 2008

(87) PCT Pub. No.: WO2007/100277
PCT Pub. Date: Sep. 7, 2007

(65) Prior Publication Data
US 2009/0171425 A1    Jul. 2, 2009

(51) Int. Cl.
*A61N 1/05* (2006.01)
(52) U.S. Cl. ........................ 607/127; 607/131
(58) Field of Classification Search .................. 607/127, 607/128, 131
See application file for complete search history.

(56) References Cited

U.S. PATENT DOCUMENTS

| | | | |
|---|---|---|---|
| 4,000,745 A | 1/1977 | Goldberg | |
| 5,431,649 A * | 7/1995 | Mulier et al. | 606/41 |
| 5,476,502 A | 12/1995 | Rubin | |
| 6,501,994 B1 | 12/2002 | Janke et al. | |
| 7,177,704 B2 | 2/2007 | Laske et al. | |
| 2004/0133259 A1 | 7/2004 | Janke et al. | |
| 2005/0070985 A1 | 3/2005 | Knapp et al. | |
| 2005/0251240 A1 * | 11/2005 | Doan | 607/127 |
| 2006/0122682 A1 | 6/2006 | Sommer et al. | |

* cited by examiner

*Primary Examiner* — Niketa Patel
*Assistant Examiner* — Alyssa M Alter
(74) *Attorney, Agent, or Firm* — Schiff Hardin LLP

(57) ABSTRACT

A medically implantable lead configured for insertion into a human or animal body to be attached in the body with its distal end to tissue inside the body, as a rotatable helix at a distal end thereof that can be screwed into the tissue. The helix serves as an attachment of the lead to the tissue as well as a conductor for conducting electrical signals to the tissue through electrically conducting surfaces on the helix. The surfaces of the helix are partly insulated so as to restrict the conducting of signals between the helix and the tissue to desirable regions. The surfaces of the helix facing inwardly, toward an inner bore of the helix, are electrically insulated. In a method for manufacturing such a lead, the wire forming the helix has protrusions in desired areas and the wire including the protrusions is coated with an electrically insulating layer. The protrusions are uncovered from the insulating layer in desired regions.

6 Claims, 2 Drawing Sheets

IMPLANTABLE MEDICAL LEAD AND METHOD FOR THE MANUFACTURE THEREOF

BACKGROUND OF THE INVENTION

1. Field of the Invention

The invention relates to a medical implantable lead adapted to be inserted into a human or animal body and attached, with its distal end, to tissue inside the body, of the type having a rotatable helix in the distal end that can be screwed into the tissue, the helix being adapted to serve as an attachment of the lead to the tissue as well as to serve as a conductor for conducting of electrical signals to the tissue through electrical conducting surfaces on the helix, wherein the surfaces of the helix being partly insulated to restrict the conducting of signals between the helix and the tissue to desirable regions.

The invention also relates to a method for manufacturing of a helix for a medical implantable lead.

2. Description of the Prior Art

A medical implantable lead of the above kind may be used for different purposes, such as for connection to a pacemaker for monitoring and pacing the activity of a human heart, or for use as a nerve stimulator, or for connection to a diagnostic device for monitoring and stimulating the activity of an arbitrary organ in a human or animal body.

Such a diagnostic and therapeutic device is often implanted into the body to perform its function during a long time. In such cases the electrical power source for power supply to the lead, is in form of at least one battery positioned in the device. In order to prolong the battery life, and hence extend the time interval between each replacement of the implanted device, it is advantageous to restrict the power consumption as much as possible. The current drain from the lead has a great influence on the overall power consumption and if the transition impedance from the helix in the lead to body tissue is increased, the current drain will be reduced. One way to achieve this is to restrict the electrically conductive surfaces on the helix by applying an insulating layer on parts of the surface thereof.

In U.S. Pat. No. 6,501,994 and United States Patent Application Publication No. 2004/0133259 the above problem has been recognized and consequently the implantable leads disclosed in these publications, are provided with helixes whose surfaces have been provided with an insulating coating over a portion of the helix. However, the current drain from these helixes is still considerable, and it would be favorable to further restrict the current drain to allow a more effective utilization of the electrical power.

U.S. Pat. No. 5,476,502 discloses a defibrillation electrode in the shape of a helix that, although a part of the inside of the helix is provided with an insulating layer, is designed to have a conducting surface that is as large as possible an hence with a low impedance.

SUMMARY OF THE INVENTION

An object of the present invention is to provide an improved medical implantable lead. More precisely, it is an object of the invention to further restrict the current drain from medical implantable leads in comparison to leads known in the art, and provide a medical implantable lead which utilizes the current emitted from the helix in a more effective way.

The invention also relates to a method for manufacturing a medical implantable lead of the above kind. An object of the method is to manufacture the lead in an effective, reliable and cost effective way.

Accordingly, the present invention is based on the insight that the above object may be achieved by a medical implantable lead having a helix, of which at least the surfaces facing inwards toward an inner bore of the helix are electrically insulated. The reason for this is that it has been found, according to the invention, that any current emitted from the inward facing surfaces of the helix has no or only an insignificant effect on the tissue. Usually it is desirably to distribute the emitted current as much as possible in an appropriate layer or region of the surrounding tissue to ensure a maximum effect in relation to the amount of current emitted. Any current emitted from the inward facing surfaces of the helix, is however "trapped" inside the helix and will to a major extent only have a local influence on the tissue.

Within the scope of this general inventive idea, the invention may be realized in many different ways. In one embodiment, the surfaces of the helix, having an arbitrary cross sectional form, which in a cross section of the helix is facing inwardly toward an inner bore of the helix and positioned within lines, each constituting a normal to a tangent of the helix surface and touching an inner surface of an adjacent coil of the helix, are electrically insulated.

In another embodiment, the inner and lateral surfaces of the helix, having an arbitrary cross sectional form, which in a cross section of the helix is facing inwardly toward an inner bore of the helix and laterally toward adjacent coils of the helix and positioned within lines, each constituting a normal to a tangent of the inner surface and touching an outer surface of an adjacent coil of the helix, are electrically insulated. Consequently, according to this embodiment, also the surfaces of the helix facing adjacent coils of the helix are electrically insulated.

According to yet another embodiment of the helix having a generally rectangular or flattened cross sectional form, the inner surfaces and lateral surfaces of the helix which, in a cross section of the helix, is facing inwards toward a bore of the helix and toward adjacent coils of the helix, respectively, are electrically insulated. Consequently, only the outward facing surfaces of the helix are provided with electrically conducting surfaces.

Moreover, in a preferred embodiment, not all of the areas of the outward facing surfaces of the helix are electrically conductive. Instead the outward facing surfaces of the helix are provided with electrically insulated regions as well as conductive regions in a desirable configuration. For example, when using a lead where the helix is extendable out from the bore of a tubular or sleeve formed tip, usually not the entire helix is extendable. Instead a part of the helix will remain inside the sleeve and it is unfavorably that any surfaces of that part are made electrically conducting. Therefore, in one embodiment, at least this part of the helix is completely insulated.

The tissue to be stimulated or monitored often has an external mucous membrane which is electrically inactive and therefore preferably also a part of the helix outside the tubular tip, having a length of at least 0.3 mm and preferably between 0.3-1.0 mm, is completely insulated. For similar reasons, since the distal end portion of the helix may be extended past the electrically active layer of the tissue and into a second inactive layer, e.g. into the opposite inactive mucous membrane of a heart wall, also a distal end portion of between 0.3-1.0 mm of the helix is completely insulated in one embodiment.

The one or more regions of the helix that are electrically conductive may be electrically conductive over a comparatively large, continuous surface. However, in order to increase the transition impedance between the helix and the tissue, the electrically conductive regions, in an alternative embodiment, are formed with alternating conducting surfaces as well as insulated surfaces in a desired pattern. In this way the current emission will be concentrated to the limited electrically conductive surfaces. The conductive pattern may be arbitrary formed. However, it has proved advantageous if the pattern is in form of protrusions, which project from the surface and which preferably are formed with sharp edges or points. In this way the current emission will be advantageously locally concentrated to the edges and points. In a preferred embodiment, the protrusions are pyramid shaped, having three or more essentially plane surfaces as well as the same number of edges and one tip, or shaped as a truncated pyramid or conical shaped with no edges but one tip.

For pacemaker applications, the protrusions may preferably have an area of 0.005 mm$^2$ to 0.1 mm$^2$, typically about 0.04 mm$^2$, and a center to center spacing of 0.1 mm to 0.5 mm, preferably about 0.3 mm, corresponding to the length of one to three muscle cells in the heart. In this way the possibility for each protrusion to stimulate or monitor at least one muscle cell is enhanced, although the possibility for two or more adjacent protrusions to stimulate the same muscle cell is eliminated.

A helix according to the invention can be built up and manufactured in many different ways. The cross sectional shape may be for example circular or rectangular. Normally, when manufacturing a helix having a rectangular cross section and electrically conducting protrusions, it is preferred to start from a straight metal wire, of e.g. tantalum, having a circular cross section, which is flattened to a somewhat rectangular shape and processed to form protrusions on one side or section of its circumference. Thereafter the wire is provided with an electrically insulating layer, e.g. of non-conductive diamond-like carbon (DLC), which is coated over its entire external surface. Subsequently, the insulating layer is removed from the protrusion in one or more desirable regions of the wire. This may be effected in different ways. For example, the wire may be rolled between two rollers of which one has a comparably soft layer into which the protrusions will be pressed during the rolling such that the insulating layer will be abraded from the protrusions. If the layer is made of DLC another way might be to remove the layer over the protrusions with a laser beam, which would have the advantage that the removed carbon would be turned into carbon dioxide with no other residues. If desired, the protrusions may then be provided with a layer of tantalum oxide (Ta$_2$O$_5$) or another material with corresponding properties, which will yield a highly capacitive transition zone combined with a high faradic resistance. After this, the wire will be formed into a helix, having the protrusions facing outwards, and cut into pieces of suitable lengths.

However, it would also be possible to form the structural body of the helix of an electrically insulating material, e.g. carbon fiber reinforced plastics, which is provided with an electrically conducting lead, e.g. a metal wire positioned inside the helix. When forming the electrically conducting protrusions onto the helix by any suitably method, the protrusions at the same time are connected to the electrically conducting lead.

Within the scope of the associated claims, it is obvious that the invention may be modified in many different ways and it is to be understood that the hereinafter described and in the drawings illustrated embodiments of the invention, is given only for purpose of exemplifying. For example, the lead hereinafter described, is provided with a tubular distal end, into which a helix may be retracted in an inactive state, and extendable to an active state by screw rotating the helix in relation to the tubular end. However, it should be understood that the helix also can be fixed in relation to the rest of the lead, wherein screw rotating of the helix into the tissue is accomplished by rotating the entire lead.

DESCRIPTION OF THE PREFERRED EMBODIMENTS

Figure 1:
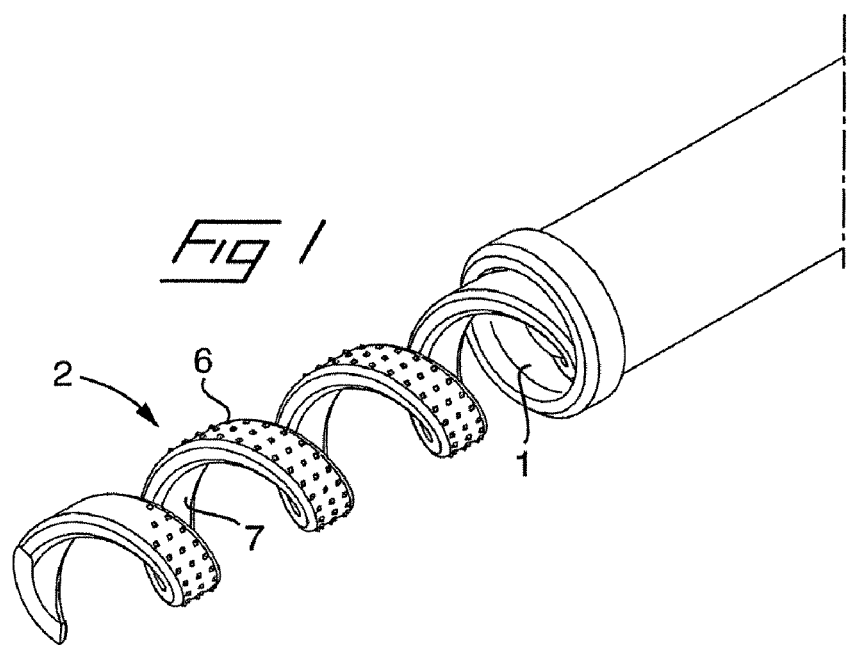
FIG. 1 is a perspective view of a distal portion of a lead embodying a helix, in accordance with the present invention.

FIG. 1 shows, in a perspective view, a distal portion of an electrical lead for a pacemaker application. The lead is tubular or sleeve formed in its distal end, defining a bore 1 into and out from which a helix 2 is retractable and extendable by screw rotating it by means of some suitable means known in the art, however not shown in the drawings.

According to the invention, the inward facing surfaces of the circumference of the helix are electrically insulated. The outward facing surfaces of the helix, on the other hand, may optionally be electrically conducting over a continuous area and/or in restricted areas and/or in spots in an arbitrary pattern.

Figure 2:
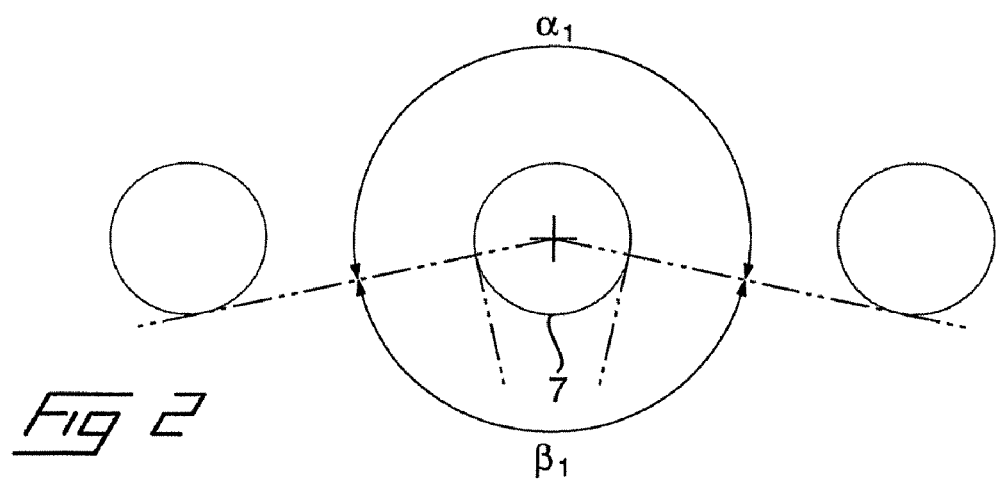
FIG. 2 is a cross section through three adjacent coils of the helix, illustrating a section, according to a first embodiment, of a helix wire circumference to be provided with electrically conducting surfaces and insulating surfaces, respectively.
Figure 3:
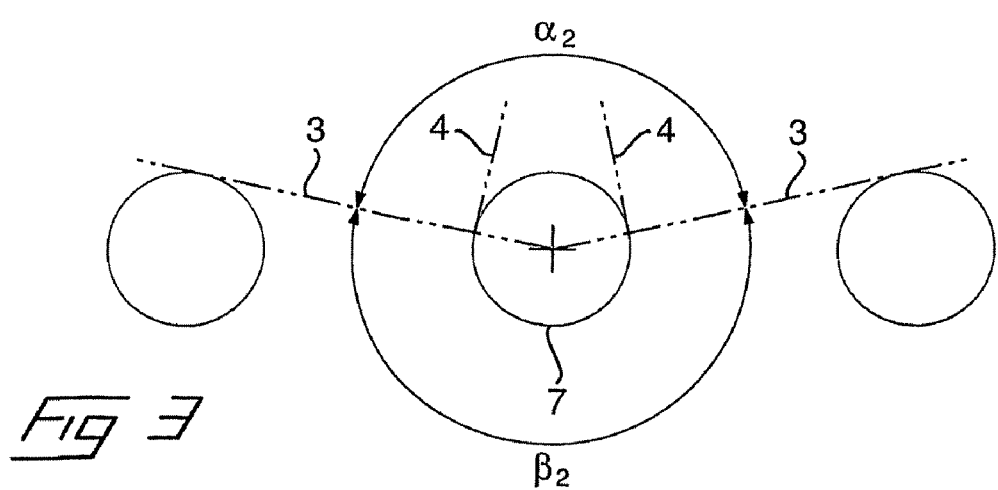
FIG. 3 shows a cross section similar to FIG. 2, illustrating a helix section, according to a second embodiment, to be provided with electrically conducting surfaces and insulated surfaces, respectively.

In FIGS. 2 and 3 illustrated are two alternative definitions of the surfaces of a helix wire which are adapted to be electrically conductive, or provided with electrically conducting spots in a desired pattern, and electrically insulated, respectively. It is to be understood, according to the definition, that the cross sectional shape of the wire may be arbitrary although it is shown as being circular in the drawings. According to a first definition, illustrated in FIG. 2, the surfaces of the helix which, in a cross section of the helix wire, are facing inwards toward a bore of the helix and positioned within lines 3 constituting a normal to a tangent 4 of the inner surface and touching an inner surface of adjacent coils of the helix, are electrically insulated. I.e. the surfaces within the angle segment $\alpha_1$ are electrically conducting, either completely or partly in a desired pattern, wherein the surfaces 7 within the angle segment $\beta_1$ are electrically insulating.

According to a second definition, illustrated in FIG. 3, the inner surfaces of the helix which, in a cross section of the helix, are facing inwards and laterally toward the bore as well as adjacent coils of the helix and positioned within lines 3 constituting a normal to a tangent 4 of the inner surface and touching an outer surface of adjacent coils of the helix, are electrically insulated. I.e. the surfaces within the angle segment $\alpha_2$ are electrically conducting, either completely or partly in a desired pattern, wherein the surfaces 7 within the angle segment $\beta_2$ are electrically insulating.

Figure 4:
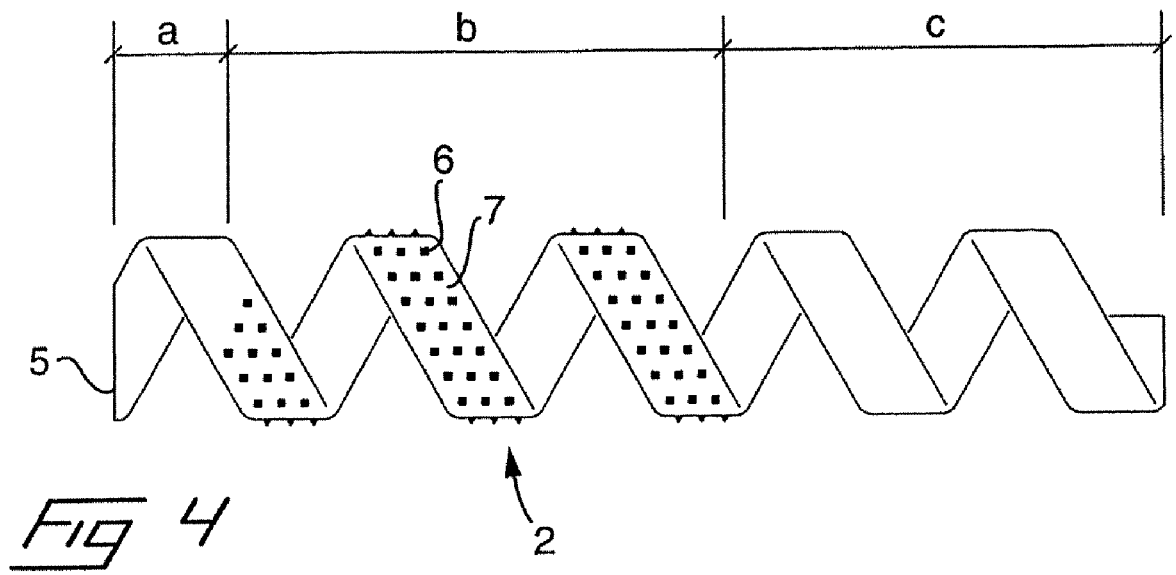
FIG. 4 is a side view of the helix provided with electrically conducting regions as well as electrically insulated regions on the outwardly facing surfaces thereof.

Moreover, the outward facing surfaces of the helix may be divided into regions being partly or completely electrically conducting and regions being completely electrically insulated. This is illustrated in FIG. 4 where a distal portion a, including a tip 5 of the helix 2, is completely electrically insulated. An intermediate portion b of the helix, on the other hand, is provided with electrically conducting spots 6 and surrounding insulated surfaces 7 in a desired pattern. Also a proximal portion c of the helix is electrically insulated. This portion of the helix is located, when mounted to the lead, inside the bore 1 of the lead and attached to a rotatable shaft. Also a small portion of the helix being located immediately outside of the bore in an extended state of the helix is in a preferred embodiment completely insulated. This latter portion may be at least 0.3 mm and preferably between 0.3 to 1.0 mm.

Figure 5:
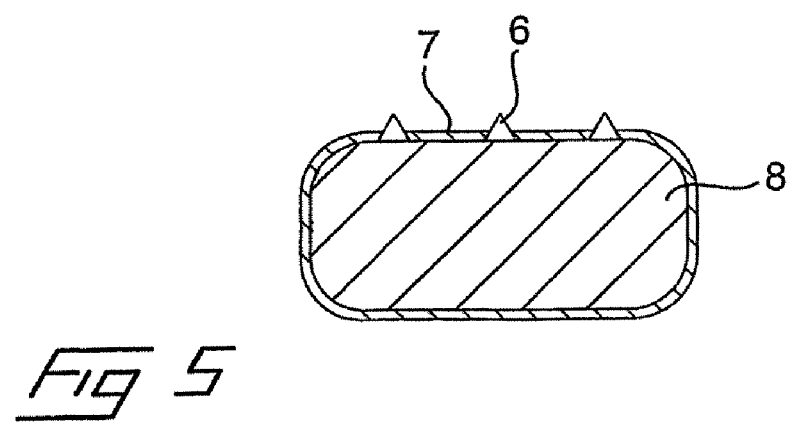
FIG. 5 is a cross section through a helix wire having a pattern of electrically conducting protrusions.

As is evident, the one or more electrically conducting regions b of the outward facing surfaces of the helix 2 are in a preferred embodiment not electrically conducting over the entire area of that region. Instead, the electrically conducting region is provided with electrically conducting spots 6 surrounded by electrically insulated surfaces 7 in a desired pattern. In FIG. 5, one embodiment of such a partial conducting region is depicted in a cross section. Here the electrically conducting spots are protrusions having pyramidal shape with a square base, which protrude from an electrically conducting base material 8 of the helix through an electrically insulating layer 7 surrounding the helix cross section.

Although modifications and changes may be suggested by those skilled in the art, it is the intention of the inventor to embody within the patent warranted heron all changes and modifications as reasonably and properly come within the scope of his contribution to the art.

I claim as my invention:

1. A medical implantable lead being adapted to be inserted configured for insertion into a human or animal body and attached, with a distal end, to tissue inside the body, comprising a rotatable helix in the distal end which can be screwed into the tissue, the helix being adapted configured to serve as an attachment of the lead to the tissue as well as to serve as a conductor for conducting of electrical signals to the tissue through electrical conducting surfaces on the helix, the helix being having surfaces that are partly insulated to restrict the conducting of signals between the helix and the tissue to desirable regions, and at least the surfaces of the helix which, in a cross section of the helix, are positioned within lines constituting a normal to a tangent of the inner surface and touching an inner surface of adjacent coils of the helix, being provided with an insulating layer, said helix having external surface with electrically insulated regions and electrically conducting regions, said electrically conducting regions of the external surface of the helix having conducting structures as well as insulated surfaces arranged in an electrically conducting pattern wherein said electrically surfaces are formed as electrically conducting protrusions that project from said insulated surfaces.

2. A medical implantable lead according to claim 1, the helix has inner surfaces which, in a cross section of the helix, are positioned within lines constituting a normal to a tangent of the inner surface and touching an outer surface of adjacent coils of the helix, are provided with an insulating layer.

3. A medical implantable lead according to claim 2, the helix is formed of a wire having an essentially rectangular cross section, wherein a side of the wire facing outwardly, is provided with electrically conducting surfaces whereas the surfaces on the remaining sides are electrically insulated.

4. A medical implantable lead according to claim 1, wherein the protrusions comprise sharp edges or points.

5. A medical implantable lead according to claim 1 wherein the protrusions have pointed tips.

6. A medical implantable lead according to claim 1 wherein the protrusions a form selected from the group consisting of pyramids and truncated pyramids.

* * * * *